United States Patent
Zhang et al.

(10) Patent No.: US 10,646,649 B2
(45) Date of Patent: May 12, 2020

(54) INFUSION DEVICES AND FLUID IDENTIFICATION APPARATUSES AND METHODS

(71) Applicant: MEDTRONIC MINIMED, INC., Northridge, CA (US)

(72) Inventors: Guangping Zhang, Calabasas, CA (US); Sarnath Chattaraj, Simi Valley, CA (US); Anuradha Biswas Bhatia, Los Angeles, CA (US); Maria C. LoVerme, Simi Valley, CA (US); Afshin Bazargan, Simi Valley, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

(21) Appl. No.: 15/438,601

(22) Filed: Feb. 21, 2017

(65) Prior Publication Data

US 2018/0236169 A1    Aug. 23, 2018

(51) Int. Cl.
*A61M 5/172* (2006.01)
*A61M 39/20* (2006.01)
(Continued)

(52) U.S. Cl.
CPC .......... *A61M 5/172* (2013.01); *A61M 39/20* (2013.01); *G01N 21/3577* (2013.01);
(Continued)

(58) Field of Classification Search
CPC .. A61M 5/172; A61M 39/20; A61M 2205/50; A61M 2205/52;
(Continued)

(56) References Cited

U.S. PATENT DOCUMENTS

| 3,631,847 A | 1/1972 | Hobbs, II |
|---|---|---|
| 4,212,738 A | 7/1980 | Henne |

(Continued)

FOREIGN PATENT DOCUMENTS

| DE | 4329229 | 3/1995 |
|---|---|---|
| EP | 0319268 | 11/1988 |

(Continued)

OTHER PUBLICATIONS

PCT Search Report (PCT/US02/03299), dated Oct. 31, 2002, Medtronic Minimed, Inc.

(Continued)

*Primary Examiner* — Amber R Stiles
(74) *Attorney, Agent, or Firm* — Lorenz & Kopf, LLP

(57) ABSTRACT

Medical devices and methods and apparatuses for identifying fluids in a conduit of a device are provided. An exemplary apparatus for identifying an infusate in a conduit of an infusion device includes a transmitter element for transmitting a beam of energy for interaction with the infusate. Further, the apparatus includes a receiver element for receiving a signal from the beam of energy after interaction with the infusate. Also, the apparatus includes an identifier element coupled to the receiver element for analyzing the signal to identify the infusate. The transmitter element and receiver element may form a spectroscopy device and may transmit and receive a beam of infrared light or near infrared light.

9 Claims, 8 Drawing Sheets

(51) Int. Cl.
*G01N 21/3577* (2014.01)
*G01N 21/359* (2014.01)
*G01N 21/33* (2006.01)

(52) U.S. Cl.
CPC ........... *A61M 2205/3313* (2013.01); *A61M 2205/3569* (2013.01); *A61M 2205/50* (2013.01); *A61M 2205/52* (2013.01); *G01N 21/33* (2013.01); *G01N 21/359* (2013.01)

(58) Field of Classification Search
CPC .. A61M 2205/3569; A61M 2205/3313; G01N 21/359; G01N 21/3577; G01N 2201/061
See application file for complete search history.

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |

(56) References Cited

U.S. PATENT DOCUMENTS

| | | |
|---|---|---|
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,323,142 B2 | 1/2008 | Pendo et al. |
| 7,365,847 B2 | 4/2008 | Auton et al. |
| 7,396,330 B2 | 7/2008 | Banet et al. |
| 7,402,153 B2 | 7/2008 | Steil et al. |
| 7,621,893 B2 | 11/2009 | Moberg et al. |
| 8,674,288 B2 | 3/2014 | Hanson et al. |
| 2001/0044731 A1 | 11/2001 | Coffman et al. |
| 2002/0013518 A1 | 1/2002 | West et al. |
| 2002/0022855 A1 | 2/2002 | Bobroff et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0193453 A1* | 9/2004 | Butterfield ............ A61M 5/172 705/2 |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |
| 2009/0131861 A1* | 5/2009 | Braig ................... A61B 5/1427 604/66 |
| 2010/0121170 A1* | 5/2010 | Rule ..................... A61B 5/1427 600/365 |
| 2011/0009800 A1* | 1/2011 | Dam .................... A61M 1/3626 604/6.16 |
| 2012/0232362 A1* | 9/2012 | Gable ............... A61B 5/150755 600/310 |
| 2013/0204227 A1* | 8/2013 | Bochenko ........... G06F 19/3456 604/506 |
| 2014/0128960 A1 | 5/2014 | Greenslet et al. |

FOREIGN PATENT DOCUMENTS

| | | | |
|---|---|---|---|
| EP | 0806738 | | 11/1997 |
| EP | 0880936 | | 12/1998 |
| EP | 1338295 | | 8/2003 |
| EP | 1631036 | A2 | 3/2006 |
| GB | 2218831 | | 11/1989 |
| WO | WO 96/20745 | | 7/1996 |
| WO | WO 96/36389 | | 11/1996 |
| WO | WO 96/37246 | A1 | 11/1996 |
| WO | WO 97/21456 | | 6/1997 |
| WO | WO 98/20439 | | 5/1998 |
| WO | WO 98/24358 | | 6/1998 |
| WO | WO 98/42407 | | 10/1998 |
| WO | WO 98/49659 | | 11/1998 |
| WO | WO 98/59487 | | 12/1998 |
| WO | WO 99/08183 | | 2/1999 |
| WO | WO 99/10801 | | 3/1999 |
| WO | WO 99/18532 | | 4/1999 |
| WO | WO 99/22236 | | 5/1999 |
| WO | WO 00/10628 | | 3/2000 |
| WO | WO 00/19887 | | 4/2000 |
| WO | WO 00/48112 | | 8/2000 |
| WO | WO 02/058537 | A2 | 8/2002 |
| WO | WO 03/001329 | | 1/2003 |
| WO | WO 03/094090 | | 11/2003 |
| WO | WO 2005/065538 | A2 | 7/2005 |
| WO | WO-2017002023 | A2 * | 1/2017 ............. G01N 15/10 |

OTHER PUBLICATIONS (Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.

(56) References Cited

OTHER PUBLICATIONS

Brackenridge B P (1992). Carbohydrate Gram Counting a Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting a Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual. (Publication or release date no later than Nov. 2007).
Disetronic H-TRON® plus Quick Start Manual. (Publication or release date no later than Nov. 2007).
Disetronic My Choice H-TRONplus Insulin Pump Reference Manual. (Publication or release date no later than Nov. 2007).
Disetronic H-TRON®plus Reference Manual. (Publication or release date no later than Nov. 2007).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analylica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263. (Publication or release date no later than Nov. 2007).
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD. et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.

(56) References Cited

OTHER PUBLICATIONS

Mckean, Brian. D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.

Monroe, D., "Novel Implantable Glucose Sensors," ACL, Dec. 1989, pp. 8-16.

Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.

Moussy, Francis, et al., "Performance of Subcutaneously Implanted Needle-Type Glucose Sensors Employing a Navel Trilayer Coating," Analytical Chemistry, vol. 65, No. 15, Aug. 1, 1993, pp. 2072-2077.

Nakamoto, S., et al., "A Lift-Off Method for Patterning Enzyme-Immobilized Membranes in Multi-Biosensors," Sensors and Actuators 13, 1988, pp. 165-172.

Nishida, Kenro, et al., "Clinical applications of teh wearable artifical endocrine pancreas with the newly designed needle-type glucose sensor," Elsevier Sciences B.V., 1994, pp. 353-358.

Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, el al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Disaccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators. vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

INFUSION DEVICES AND FLUID IDENTIFICATION APPARATUSES AND METHODS

TECHNICAL FIELD

Embodiments of the subject matter described herein relate generally to medical devices, and more particularly, embodiments of the subject matter relate to the identification of fluids for delivery from infusion devices.

BACKGROUND

Infusion pump devices and systems are relatively well known in the medical arts, for use in delivering or dispensing a fluid agent or infusate, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

In practice, it is desirable to facilitate preparation of infusate for delivery to a patient or user. Specifically, there is a desire to make the process of preparing the infusate quicker. Typically, a user must use a syringe to withdraw the fluid agent from a larger receptacle and fill a device reservoir. Then, the user must ensure that there are no bubbles or other foreign matter in the device reservoir before coupling the device reservoir with the infusion pump device.

Thus, there is a desire to utilize pre-filled and packaged reservoirs or cartridges with infusion pump devices. Such reservoirs may be filled and packaged in an automated system and shipped to users for convenient use. However, with pre-filled and packaged reservoirs, there is a danger that a user may couple to the infusion pump device an infusate that is different from the infusate that is intended to be delivered. For example, the pre-filled and packaged reservoir may contain a different medication than the intended infusate, or may include the correct medication but in a different concentration than intended. In either case, the delivery of an incorrect infusate may cause severe injury or death to the patient.

Accordingly, there is a need to accurately identify the infusate for delivery from infusion devices. Further, there is a need to provide an automated apparatus and method for examining a fluid in an infusion device that satisfies the various requirements that may be imposed.

BRIEF SUMMARY

Medical devices and methods and apparatuses for identifying fluids in a conduit of a device are provided. An embodiment of an apparatus for identifying an infusate in a conduit of an infusion device includes a transmitter element for transmitting a beam of energy for interaction with the infusate. Further, the apparatus includes a receiver element for receiving a signal from the beam of energy after interaction with the infusate. Also, the apparatus includes an identifier element coupled to the receiver element for analyzing the signal to identify the infusate. The transmitter element and receiver element may form a spectroscopy device and may transmit and receive a beam of infrared light or near infrared light.

In another embodiment, a medical device includes a reservoir for holding a fluid and a conduit for dispensing the fluid from the reservoir. Further, the medical device includes a spectroscopy device for examining the fluid.

Another embodiment provides a method for identifying a fluid for delivery to a body of a user. The method includes transmitting a beam of energy into contact with the fluid. Also, the method includes receiving a signal from the beam of energy after interaction with the fluid. Further, the method includes analyzing the signal to identify the fluid.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
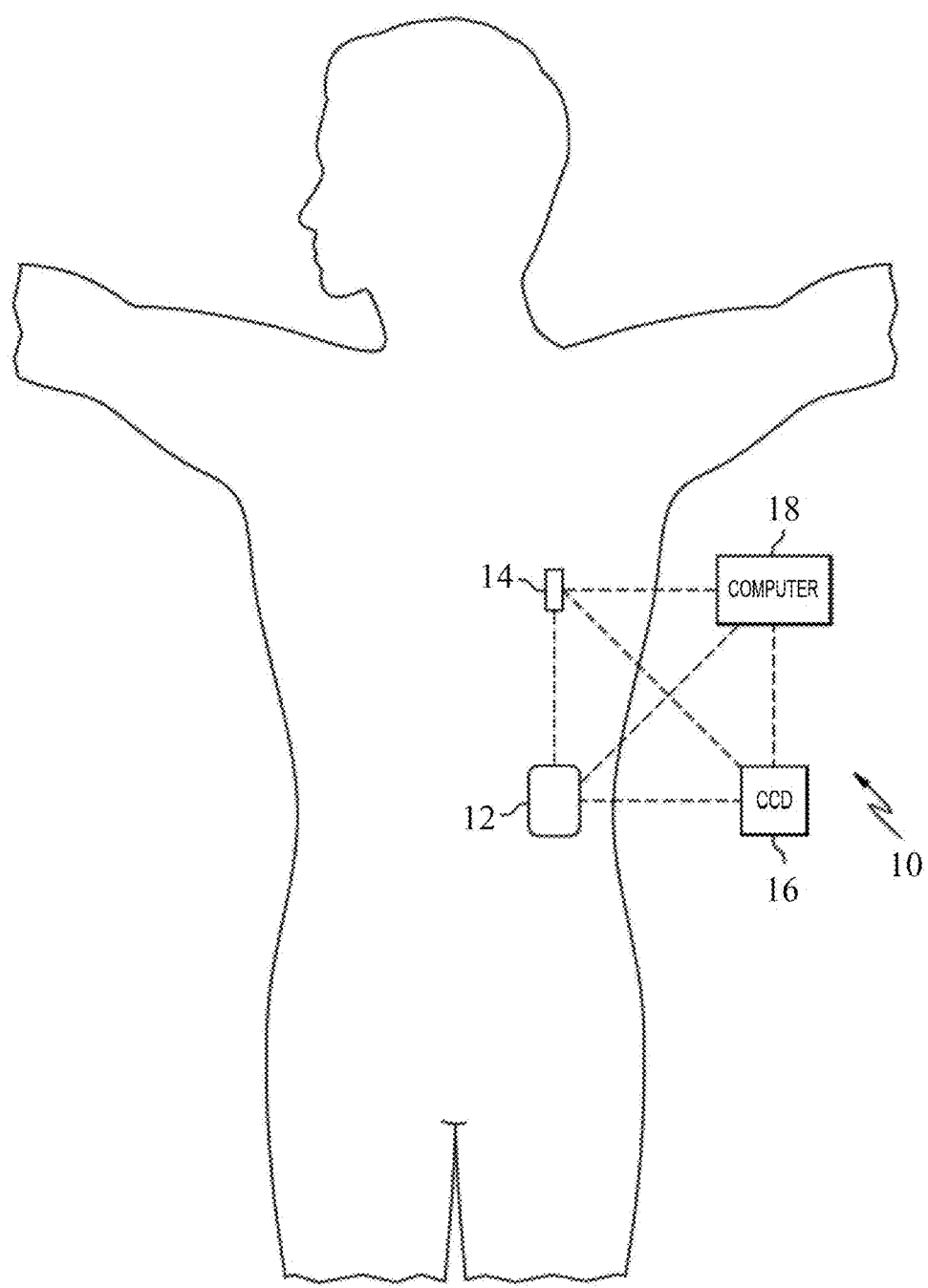
FIG. 1 depicts an infusion media delivery system for use by a patient in accordance with an embodiment herein.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to infusion systems including a fluid infusion device having an apparatus for identifying the infusate or infusion media that is prepared for delivery to the user or patient. Embodiments provide for automated examination of the infusate to ensure that the proper infusate and the proper concentration of the infusate are coupled to the fluid infusion device. In exemplary embodiments, a transmitter and receiver pair or a combined transmitter and receiver, i.e., transceiver, is utilized to direct a beam of energy at the infusate. The beam of energy contacts and interacts with matter in the beam path and absorptive and/or reflectance spectroscopy analysis may be used to identify that material by analyzing the energy transfer between the beam of energy and the matter.

The beam of energy may be in the ultraviolet (UV), near-infrared (NIR), or infrared (IR) energy range. Radiation referred to as ultraviolet defines the wavelength of from 10 nm to 400 nm while radiation referred to as near-infrared and infrared defines the wavelength range of from about 0.8 to about 25 um. Molecules can absorb such energy without later remission by exciting certain vibrational frequencies. Molecules absorb the frequencies of polychromatic light that correspond to its molecular vibrational transitions.

The energy interacts with the fluid, i.e., the energy is absorbed, refracted and/or reflected by the fluid, and with undesired bubbles or foreign matter, such as fibrils, in the fluid. Therefore, the beam is altered by the fluid and by any undesired bubbles or foreign matter therein. The altered beam may be considered to be a signal indicative of the media through which the energy passed or from which the energy was reflected. In an exemplary embodiment, the signal is captured by the receiver and is analyzed. Analysis of the signal reveals whether the proper infusate and the proper concentration of the infusate are coupled to the fluid infusion device. For example, a spectrum of frequencies or wavelengths of the signal may be compared to known spectra of frequencies or wavelengths of medications at specific concentrations, air bubbles, or foreign materials to identify the analyzed infusate, and to identify whether air or foreign matter is present in the analyzed infusate. In an exemplary embodiment, the signal analyzed by the receiver is may be an electric or intensity reading at one or more wavelengths or may be a spectra over any selected wavelength range, such as from about 0.2 to about 16 μm.

Using UV/NIR/IR spectroscopy allows for differentiation of liquid infusate compositions from the polymeric materials used in the fluid delivery device, i.e., the polypropylene reservoir, polycarbonate cap, and polyurethane/polypropylene tubing. Thus, the liquid infusate may be spectroscopically analyzed and compared to other previously tested compositions and concentrations to identify the analyzed infusate.

The disclosure relates generally to delivery devices, systems and methods for delivering infusate or infusion media, such as a drug, to a recipient, such as a medical patient. In particular embodiments, a delivery device includes a disposable portion that secures to the recipient and that may be readily disposed of after it has been in use for a period of time. Such embodiments may be configured to provide a reliable, user-friendly mechanism to secure the delivery device to a patient for delivery of fluidic infusion media to the patient. Embodiments may be configured with feature that enhance the ease by which patients may secure the delivery device to the patient's skin and further features that enhance the ease by which patients may fill, re-fill or replace spent infusion media.

While embodiments are described herein with reference to an insulin delivery example for treating diabetes, other embodiments may be employed for delivering other infusion media to a patient for other purposes. For example, further embodiments may be employed for delivering other types of drugs to treat diseases or medical conditions other than diabetes, including, but not limited to drugs for treating pain or certain types of cancers, pulmonary disorders or HIV. Thus, the infusate may be insulin, HIV drugs, drugs to treat pulmonary hypertension, iron chelation drugs, pain medications, anti-cancer treatments, medications, vitamins, hormones, or the like. Further embodiments may be employed for delivering media other than drugs, including, but not limited to, nutritional media including nutritional supplements, dyes or other tracing media, saline or other hydration media, or the like.

A generalized representation of an infusion media delivery system 10 is shown in FIG. 1, wherein the system includes an infusion or delivery device 12 configured according to embodiments described herein. In the illustrated embodiment of FIG. 1, the delivery device 12 is designed as a portable medical device suitable for infusing an infusate, i.e., a fluid, a liquid, a gel, or other agent, into the body of a user.

The infusion media delivery system 10 may also include other components coupled for communication with the delivery device 12, including, but not limited to, a sensing arrangement 14 such as a sensor or monitor, a command control device (CCD) 16, and a computer 18. Each of the CCD 16, the computer 18 and the delivery device 12 may include receiver or transceiver electronics that allow communication with other components of the system. The delivery device 12 may include electronics and software for analyzing sensor data and for delivering infusion media according to sensed data and/or pre-programmed delivery routines. Some of the processing, delivery routine storage and control functions may be carried out by the CCD 16 and/or the computer 18, to allow the delivery device 12 to be made with more simplified electronics. However, in other embodiments, the infusion media delivery system 10 may comprise delivery device 12 without any one or more of the other components of the infusion media delivery system 10 shown in FIG. 1. The elements of the infusion media delivery system 10 may be similar to those described in U.S. Pat. No. 8,674,288, the subject matter of which is hereby incorporated by reference in its entirety.

In the generalized system diagram of FIG. 1, the delivery device 12 and sensor or monitor 14 are secured to a patient-user. The locations at which those components are secured to the patient-user in FIG. 1 are provided only as a representative, non-limiting example. The delivery device 12 and sensor or monitor 14 may be secured at other locations on the patient, and such locations may depend upon the type of treatment to be administered by the infusion media delivery system 10. As described in further detail below, the delivery device 12 contains a reservoir of infusate or infusion media and delivers the infusate into the patient's body in a controlled manner.

The sensing arrangement 14 generally represents the components of the fluid delivery or infusion media delivery system 10 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 14 may include electronics and enzymes reactive to a biological or physiological condition of the user, such as a blood glucose level, or the like, and provide data indicative of the blood glucose level to the infusion device 12, the CCD 16 and/or the computer 18. For example, the infusion device 12, the CCD 16 and/or the computer 18 may include a display for presenting information or data to the user based on the sensor data received from the sensing arrangement 14, such as, for example, a current glucose level of the user, a graph or chart of the user's glucose level versus time, device status indicators, alert messages, or the like. In other embodiments, the infusion device 12, the CCD 16 and/or the computer 18 may include electronics and software that are configured to analyze sensor data and operate the infusion device 12 to deliver fluid to the body of the user based on the sensor data and/or preprogrammed delivery routines. Thus, in exemplary embodiments, one or more of the infusion device 12, the sensing arrangement 14, the CCD 16, and/or the computer 18 includes a transmitter, a receiver, and/or other transceiver electronics that allow for communication with other components of the infusion media delivery system 10, so that the sensing arrangement 14 may transmit sensor data or monitor data to one or more of the infusion device 12, the CCD 16 and/or the computer 18.

Still referring to FIG. 1, in various embodiments, the sensing arrangement 14 may be secured to the body of the user or embedded in the body of the user at a location that is remote from the location at which the infusion device 12 is secured to the body of the user. In various other embodiments, the sensing arrangement 14 may be incorporated within the infusion device 12. In other embodiments, the sensing arrangement 14 may be separate and apart from the infusion device 12, and may be, for example, part of the CCD 16. In such embodiments, the sensing arrangement 14 may be configured to receive a biological sample, analyte, or the like, to measure a condition of the user.

In various embodiments, the CCD 16 and/or the computer 18 may include electronics and other components configured to perform processing, delivery routine storage, and to control the infusion device 12 in a manner that is influenced by sensor data measured by and/or received from the sensing arrangement 14. By including control functions in the CCD 16 and/or the computer 18, the infusion device 12 may be made with more simplified electronics. However, in other embodiments, the infusion device 12 may include all control functions, and may operate without the CCD 16 and/or the computer 18. In various embodiments, the CCD 16 may be a portable electronic device. In addition, in various embodiments, the infusion device 12 and/or the sensing arrangement 14 may be configured to transmit data to the CCD 16 and/or the computer 18 for display or processing of the data by the CCD 16 and/or the computer 18.

In some embodiments, the CCD 16 and/or the computer 18 may provide information to the user that facilitates the user's subsequent use of the infusion device 12. For example, the CCD 16 may provide information to the user to allow the user to determine the rate or dose of medication to be administered into the user's body. In other embodiments, the CCD 16 may provide information to the infusion device 12 to autonomously control the rate or dose of medication administered into the body of the user. In some embodiments, the sensing arrangement 14 may be integrated into the CCD 16. Such embodiments may allow the user to monitor a condition by providing, for example, a sample of his or her blood to the sensing arrangement 14 to assess his or her condition. In some embodiments, the sensing arrangement 14 and the CCD 16 may be used for determining glucose levels in the blood and/or body fluids of the user without the use of, or necessity of, a wire or cable connection between the infusion device 12 and the sensing arrangement 14 and/or the CCD 16.

In one or more exemplary embodiments, the sensing arrangement 14 and/or the infusion device 12 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153, all of which are incorporated herein by reference in their entirety. In such embodiments, the sensing arrangement 14 is configured to sense or measure a condition of the user, such as, blood glucose level or the like. The infusion device 12 is configured to deliver fluid in response to the condition sensed by the sensing arrangement 14. In turn, the sensing arrangement 14 continues to sense or otherwise quantify a current condition of the user, thereby allowing the infusion device 12 to deliver fluid continuously in response to the condition currently (or most recently) sensed by the sensing arrangement 14 indefinitely. In some embodiments, the sensing arrangement 14 and/or the infusion device 12 may be configured to utilize the closed-loop system only for a portion of the day, for example only when the user is asleep or awake.

Figure 2:
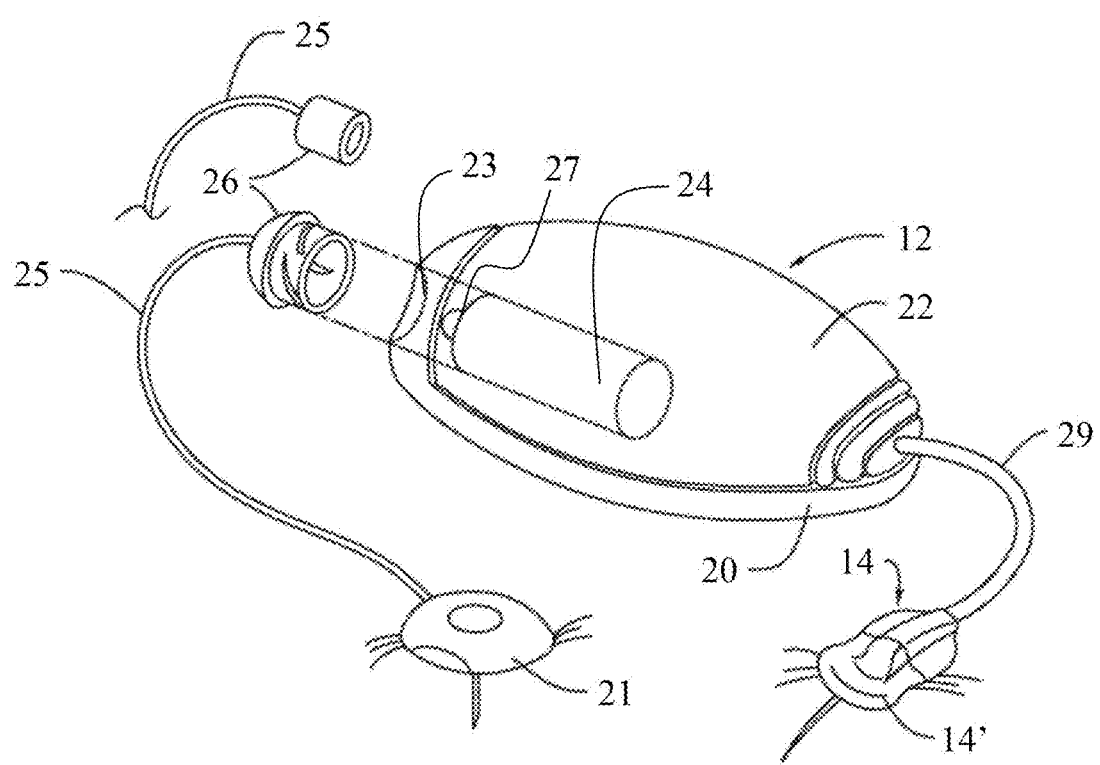
FIG. 2 depicts a plan view of an exemplary embodiment of a fluid infusion device suitable for use in the infusion system of FIG. 1.

An example of a patch-like delivery device 12 according to an embodiment is shown in FIG. 2. The delivery device 12 in FIG. 2 includes a disposable portion 20 and a durable portion 22. The disposable portion 20 may include structural elements that ordinarily contact the patient's skin or infusion media, during operation of the delivery device 12. On the other hand, the durable portion 22 may have elements (including electronics, motor components, linkage components, and the like) that do not ordinarily contact the patient or infusion media during operation of the delivery device 12. Thus, elements in the durable portion 22 of the delivery device 12 are typically not contaminated from contact with the patient or infusion media during normal operation of the delivery device 12.

In the illustrated embodiment, the disposable portion of the delivery device 12 comprises a disposable base portion 20 that supports a reservoir 24. The durable portion 22 may comprise a housing that secures onto the base portion 20 and covers the reservoir 24. The durable portion 22 may house a suitable drive device, such as an electrically operated motor (not shown in FIG. 2), and drive linkage components (not shown in FIG. 2) for driving fluid out of the reservoir 24. The durable portion 22 also may house suitable control electronics (not shown in FIG. 2) for controlling the operation of the drive device to drive fluid from the reservoir 24 in a controlled manner. Further embodiments may include communication electronics (not shown in FIG. 2) within the durable portion 22, for communicating with the sensor or monitor 14, the CCD 16, the computer 18 and/or other components of the infusion media delivery system 10.

The disposable base portion 20 has a bottom surface (facing downward and into the page in FIG. 2) that is configured to secure to a patient's skin at a desired location on the patient. A suitable adhesive may be employed at the interface between the bottom surface of the base portion 20 and the patient's skin, to adhere the base portion 20 to the patient's skin. The adhesive may be provided on the bottom surface of the base portion 20, with a removable cover layer covering the adhesive material. In this manner, a patient-user may peel off the cover layer to expose the adhesive material and then place the adhesive side of the base portion 20 against the patient's skin.

The base portion 20 may include a suitable opening or port 23 for connecting a hollow tube 25 to the reservoir 24, to convey infusion media from the reservoir 24. One end of the tube 25 may have a suitable connector 26, such as, but not limited to a Luer connector or a threaded cap connector having a hollow needle for coupling (in fluid-flow communication) to a corresponding connector 27 on the reservoir 24. Alternatively or in addition, the reservoir 24 may include a septum as part of the connector 27, for receiving an end of a hollow needle. The opening or port on the base portion 20 may be provided with corresponding connector structure, such as, but not limited to a Luer connector receptacle or a threaded receptacle shaped to receive a threaded cap connector. Other embodiments may employ other suitable connectors or connection arrangements for connecting one end of the tube 25 in fluid-flow communication with the reservoir 24.

The other end of the tube 25 may connected to a hollow needle 21 for piercing the patient's skin and conveying infusion media into the patient. The hollow needle 21 may be secured to the patient's skin, for example, by manual application or with the assistance of an insertion tool, such as, but not limited to the insertion tool described in U.S. Patent Application Publication No. 2002/0022855, titled "Insertion Device For An Insertion Set And Method Of Using The Same." In other embodiments, as described below, a hollow needle and insertion mechanism may be included within the delivery device 12, so as to avoid the need for a port 23, tube 25 and connector 26.

The durable portion 22 of the delivery device 12 includes a housing shell configured to mate with and secure to the disposable base portion 20. The durable portion 22 and base portion 20 may be provided with correspondingly shaped grooves, notches, tabs or other suitable features that allow the two parts to easily snap together, by manually pressing the two portions together in a manner well known in the mechanical arts. In a similar manner, the durable portion 22 and base portion 20 may be separated from each other by manually applying sufficient force to unsnap the two parts from each other. In further embodiments, a suitable seal, such as an o-ring seal, may be placed along the peripheral edge of the base portion 20 and/or the durable portion 22, so as to provide a seal against water between the base portion 20 and the durable portion 22.

The durable portion 22 and base portion 20 may be made of suitably rigid materials that maintain their shape, yet provide sufficient flexibility and resilience to effectively snap together and apart, as described above. The base portion 20 material may be selected for suitable compatibility with the patient's skin. For example, the base portion 20 and the durable portion 22 of the delivery device 12 may be made of any suitable plastic, metal, composite material or the like. The base portion 20 may be made of the same type of material or a different material relative to the durable portion 22. The base portion and durable portions may be manufactured by injection molding or other molding processes, machining processes or combinations thereof.

For example, the base portion 20 may be made of a relatively flexible material, such as a flexible silicon, plastic, rubber, synthetic rubber or the like. By forming the base portion of a material capable of flexing with the patient's skin, a greater level of patient comfort may be achieved when the base portion is secured to the patient's skin. Also, a flexible base portion 20 can result in an increase in the site options on the patient's body at which the base portion 20 may be secured.

In the embodiment illustrated in FIG. 2, the durable portion 22 of the delivery device 12 is connected to sensor 14, through a sensor lead 29. Sensor 14 may comprise any suitable biological or environmental sensing device, depending upon the nature of the treatment to be administered by the delivery device 12. For example, in the context of delivering insulin to a diabetes patient, the sensor 14 may comprise a blood glucose sensor.

The sensor 14 may be an external sensor that secures to the patient's skin or, in other embodiments, may be an implantable sensor that is located in an implant site within the patient. In the illustrated example of FIG. 2, the sensor 14 is an external sensor having a disposable needle pad 14' that includes a needle for piercing the patient's skin and enzymes and/or electronics reactive to a biological condition, such as blood glucose level, of the patient. The disposable needle pad 14' may electrically contact electrical conductors in the lead 29, to convey electrical signals from the sensor 14 to suitable sensor electronics located within the durable portion 22 of the delivery device 12. The lead 29 may have any suitable length. In this manner, the delivery device 12 may be provided with sensor data from a sensor secured to the patient, at a site remote from the location at which the delivery device 12 is secured to the patient.

While the embodiment shown in FIG. 2 includes a sensor 14 connected by a lead 29 for providing sensor data to sensor electronics located within the durable portion 22 of the delivery device 12, other embodiments may employ a sensor 14 located within the delivery device 12. Yet other embodiments may employ a sensor 14 having a transmitter for communicating sensor data by a wireless communication link with to receiver electronics located within the durable portion 22 of the delivery device 12. The wireless connection between the sensor 14 and the receiver electronics in the durable portion 22 of the delivery device 12 may comprise a radio frequency RF connection, an optical connection, or another wireless suitable communication link. Further embodiments need not employ a sensor and, instead, provide infusion media delivery functions without the use of sensor data.

As described above, by separating disposable elements of the delivery device 12 from durable elements, the disposable elements may be arranged on the disposable base portion 20, while durable elements may be arranged within a separable durable portion 22. In this regard, after one (or a prescribed number) of uses of the delivery device 12, the disposable base portion 20 may be separated from the durable portion 22, so that the disposable base portion 20 may be disposed of in a proper manner. The durable portion 22 may, then, be mated with a new (un-used) disposable base portion 20 for further delivery operation with a patient.

The reservoir 24 may be supported by the disposable base portion 20 in any suitable manner. The reservoir 24 may be provided as a cartridge or generally cylindrical canister for containing fluidic infusion media. For example, the base portion 20 may be provided with projections or struts, or a trough feature for holding a cartridge-type reservoir in a manner that allows a user to readily remove the reservoir from the base portion and re-install a new or refilled reservoir, when replacement or re-filling is needed, as described with respect to further embodiments below. Alternatively, or in addition, the reservoir 24 may be secured to the base portion 20 by a suitable adhesive or other coupling structure. The reservoir 24 has a port and may be supported by the base portion 20 in a position at which a connector 26 may engage or otherwise come into fluid flow communication with the reservoir port, when the connector 26 is connected to the port 23 on the base portion 20.

The durable portion 22 of the delivery device 12 may include a motor or other force-applying mechanism, for applying a force to the infusion media within the reservoir 24 to force fluidic infusion media out of the reservoir 24 and into the needle, for delivery to the patient. For example, an electrically driven motor may be mounted within the durable portion 22 with appropriate linkage for causing the motor to operably engage a piston of the reservoir and drive the reservoir piston in a direction to cause the fluidic pressure within the reservoir 24 to increase and thereby force fluidic infusion media out of the reservoir port, into the tube 25 and needle. The motor may be arranged within the durable portion 22 and the reservoir may be correspondingly arranged on the disposable portion 20, such that the operable engagement of the motor with the reservoir piston (e.g., through appropriate linkage) occurs automatically upon the patient-user snap fitting the durable portion 22 onto the disposable portion 20 of the delivery device 12.

Figure 3:
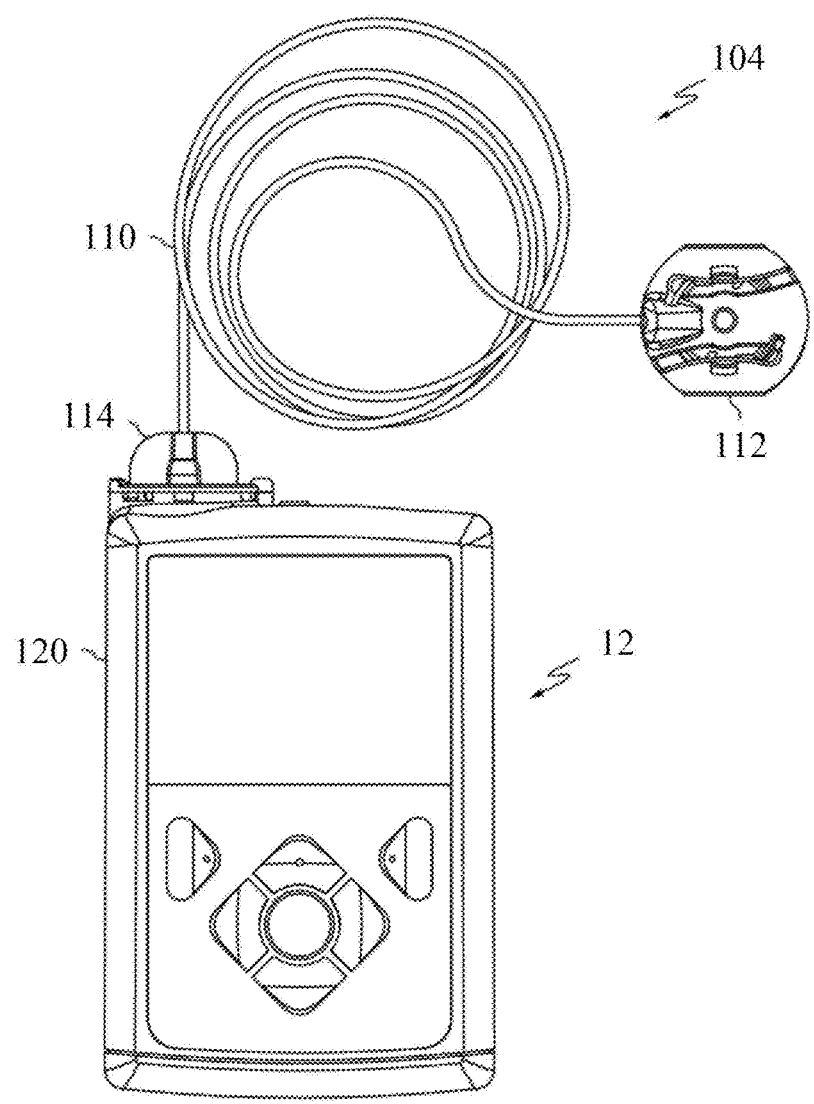
FIG. 3 depicts a plan view of an exemplary embodiment of another fluid infusion device suitable for use in the infusion system of FIG. 1.

While FIG. 2 illustrates an embodiment of a patch-like delivery device 12 for use in the fluid delivery system 10, FIG. 3 illustrates an exemplary embodiment of a fluid infusion delivery device 12 coupled with an infusion set 104 with a fluid conduit assembly for use in the fluid delivery system 10 of FIG. 1. The fluid infusion delivery device 12 accommodates a fluid reservoir (hidden from view in FIG. 3) for the infusate to be delivered to the user.

The illustrated embodiment of the infusion set 104 includes, without limitation: a length of tubing 110; an infusion unit 112 coupled to the distal end of the tubing 110; and a connector 114 coupled to the proximal end of the tubing 110. The fluid infusion delivery device 12 is designed to be carried or worn by the patient, and the infusion set 104 terminates at the infusion unit 112 such that the fluid infusion delivery device 12 can deliver fluid to the body of the patient via the tubing 110. The infusion unit 112 includes a cannula (hidden from view in FIG. 3) that is coupled to the distal end of the tubing 110. The cannula is inserted into the skin and is held in place during use of the fluid infusion delivery device 12.

The infusion set 104 defines a fluid flow path that couples a fluid reservoir to the infusion unit 112. The connector 114 mates with and couples to a section of the fluid reservoir (not shown), which in turn is coupled to a housing 120 of the fluid infusion delivery device 12. The connector 114 establishes the fluid path from the fluid reservoir to the tubing 110. Actuation of the fluid infusion delivery device 12 causes the medication fluid to be expelled from the fluid reservoir, through the infusion set 104, and into the body of the patient via the infusion unit 112 and cannula at the distal end of the tubing 110. Accordingly, when the connector 114 is installed as depicted in FIG. 3, the tubing 110 extends from the fluid infusion delivery device 12 to the infusion unit 112, which in turn provides a fluid pathway to the body of the patient.

The fluid infusion delivery device 12 includes a radio frequency (RF) antenna to support wireless data communication with other devices, systems, and/or components. The RF antenna can be located inside the housing 120 or it can be integrally formed with the housing 120. Accordingly, the RF antenna is hidden from view in FIG. 3.

Figure 4:
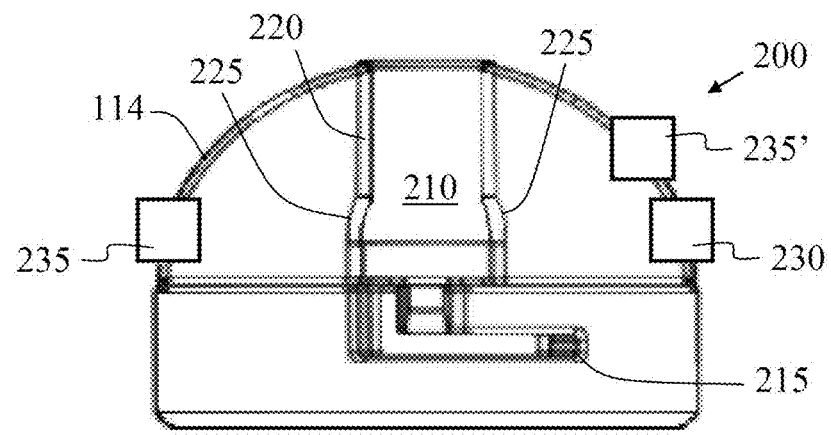
FIG. 4 depicts a plan view of an exemplary embodiment of an apparatus for examining a fluid in the fluid infusion device of FIG. 2 or 3.
Figure 5:
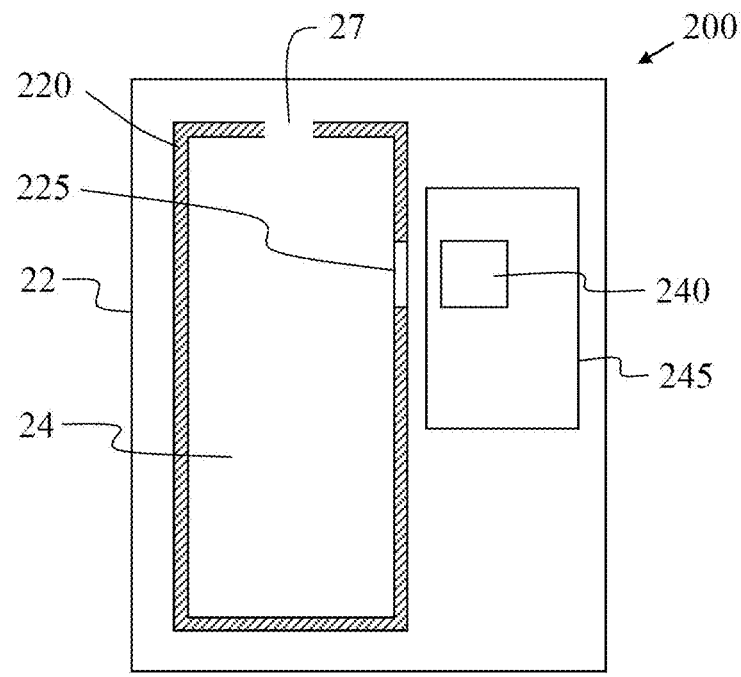
FIG. 5 depicts a plan view of another exemplary embodiment of an apparatus for examining a fluid in the fluid infusion device.

As may be understood from FIGS. 1-3, each embodiment of the fluid delivery device 12 includes a reservoir for holding an infusate and a fluid path for delivering the infusate from the reservoir to the patient. Other embodiments of fluid delivery devices 12 are contemplated herein for use with the infusate identifying apparatus and method. The reservoir and fluid path in such fluid delivery devices 12 are considered to be portions of a conduit in which the infusate is contained and flows. FIGS. 4 and 5 illustrate embodiments in which a portion of the fluid delivery device 12 is provided with an apparatus for identifying the infusate and any foreign matter within the infusate while located in the conduit.

In FIG. 4, an identifying apparatus 200 is located on or otherwise coupled to the connector 114 of the fluid delivery device of FIG. 3. It is contemplated that the identifying apparatus 200 of FIG. 4 may be utilized with other types of fluid delivery devices. As shown, the connector 114 defines a fluid path 210 in which the infusate may be contained and through which the infusate may flow. Fluid communication may be established between the fluid path 210 and the reservoir (not shown) through a coupling or fitting 215.

The fluid path 210 may be defined and bounded by a wall 220. Wall 220 may be transparent, translucent, or otherwise transmit the interrogating beam of energy (described below). An exemplary wall 220 is substantially transparent. For example, wall 220 may be formed from a transparent material such as clear polycarbonate, polypropylene, polyurethane/polypropylene, or other clear polymeric material. Alternatively or additionally, the wall 220 of the fluid path 210 may be formed with a window 225 that is transparent, translucent, or otherwise transmit the interrogating beam of energy. An exemplary transparent window 225 may be formed from clear polycarbonate, polypropylene, polyurethane/polypropylene, or other clear polymeric material.

As shown in FIG. 4, the identifying apparatus 200 includes a transmitter element 230. Transmitter element 230 may be a standalone transmitter or part of a transceiver device that transmits and receives. An exemplary transmitter element 230 is arranged to transmit a beam of energy into the fluid path 210, either through wall 220 or through a window 225 in wall 220, for interaction with an infusate contained within the fluid path 210. An exemplary transmitter element 230 is an infrared (IR), near infrared (NIR) or ultraviolet (UV) emitter and is arranged to transmit a beam of IR, NIR or UV energy into the fluid path 210. In an exemplary embodiment, the transmitter element transmits the beam of energy into the fluid orthogonally to the direction of fluid flow.

Further, the exemplary identifying apparatus 200 includes a receiver element 235. Receiver element 235 may be a standalone receiver or part of a transceiver device that transmits and receives. An exemplary receiver element 235 is arranged to receive a beam of energy from the fluid path 210, either through wall 220 or through a window 225 in wall 220. An exemplary transmitter element 230 is an infrared (IR), near infrared (NIR) or ultraviolet (UV) receiver and is arranged to receive a beam of IR, NIR or UV energy from the fluid path 210.

As shown in FIG. 4, the receiver element 235 may be located on an opposite side of the fluid path 210 from the transmitter element 230 to receive a signal, in the form of an altered beam of energy, that passes through the fluid path 210. Alternatively, a receiver element 235' may be located on the same side of the fluid path 210 as the transmitter element 230 to receive a signal, in the form of an altered beam of energy, that is reflected from the fluid path 210. The transmitter element 230 and receiver element 235 may be in wired or wireless electronic connection with receiver electronics that may communicate with sensing arrangement 14, CCD 16 or computer 18 of FIG. 1. The receiver electronics, sensing arrangement 14, CCD 16 or computer 18 may include an identifier element for analyzing an electronic representation of the signal of the altered beam of energy received by a receiver element 235.

The signal received by the receiver element 235 differs from the initial beam of energy transmitted by the transmitter element 230. Specifically, absorption and/or reflectance of radiation, as a function of frequency or wavelength, results from interaction of the beam of energy with the infusate and any foreign matter in the fluid path 210 (as well as the window 225). Therefore, the resulting beam or signal exiting the fluid path 210 includes a lower radiation intensity, particularly at specific frequencies or wavelengths. The radiation spectrum of the signal exiting the fluid path 210 provide a identifiable signature or fingerprint associated with the matter on which the beam was directed and may be used in analysis as described below. The electronic representation of the signal that is analyzed by the identifier element may include electric or intensity readings at one or more wavelengths or a spectra over an selected range of wavelengths, such as from 0.2 to 16 μm.

FIG. 5 illustrates an embodiment in which the identifying apparatus 200 is provided for use with a fluid delivery device 12 as illustrated in FIG. 2. In FIG. 5, the reservoir 24 is shown as being mounted in the durable portion 22 of the delivery device. As shown, the reservoir 24 includes a connector 27 for mating connection with the hollow tube as discussed above in relation to FIG. 2. As used herein, any of the components containing or delivering a flow of an infusate are considered a conduit.

In FIG. 5, a wall 220 bounds and defines the reservoir 24. The wall 220 may be transparent, translucent, or otherwise transmit the interrogating beam of energy as described above in relation to FIG. 4. In FIG. 5, the wall 220 is illustrated as includes a window 225 that is transparent to the intended type of interrogating beam energy and response signal energy.

Further, the fluid delivery device in FIG. 5 includes a transceiver 240 that includes both a transmitter element and a receiver element. The transceiver 240 is aligned with the window 225 so that the transceiver 240 may transmit a beam of energy through the window 225 and into contact with an infusate located in the reservoir 24, and may receive a reflected beam of energy from the infusate and through the window 225.

As further shown, the transceiver 240 is mounted to a printed circuit board (PCB) 245 that may be part of receiver electronics located within the durable portion 22. The PCB 245 may be in communication with sensing arrangement 14, CCD 16 or computer 18 of FIG. 1 through the receiver electronics. The PCB 245 may serve as an identifier element for analyzing a signal received by a receiver element of the transceiver 240. Alternatively, the sensing arrangement 14, CCD 16 or computer 18 may include an identifier element for analyzing a signal received by a receiver element of the transceiver 240. In either case, the identifier element may analyze an electronic representation of the signal that may include electric or intensity readings at one or more wavelengths or a spectra over an selected range of wavelengths, such as from 0.2 to 16 μm.

While FIG. 4 illustrates an embodiment in which the identifying apparatus 200 includes a transmitter element 230 and receiver element 235 mounted to the connector 114 and FIG. 5 illustrates an embodiment in which the identifying apparatus 200 includes a transceiver 240 that is mounted to a durable portion 22, other embodiments are contemplated. For example, the transmitter element 230 and receiver element 235 may be physically decoupled from the conduit where analysis is to be performed. Also, the elements 230 and 235 may be mounted to the wall 220 of the conduit where analysis is to be performed. Further, elements 230 and 235 may be located within the conduit where analysis is to be performed. Also, elements 230 and 235 could be formed as parts of other components within the fluid delivery device. As contemplated herein, the identifying apparatus 200, including elements 230 and 235, may be located in any suitable location along the fluid path of a fluid delivery device 12. Further, a fluid delivery device 12 may be provided with more than one identifying apparatus 200, each including elements 230 and 235. In an exemplary embodiment, each of the identifying apparatuses 200 transmits a beam of energy into the fluid orthogonally to the direction of fluid flow or to the wall of the vessel through which the fluid flows.

FIGS. 6-10 illustrate the use of transmitter elements 230 and receiver elements 235 of an identifying apparatus 100 to identify the composition and concentration of a fluid or infusate 280 within a conduit 260, such as a reservoir, hollow tube, or other fluid path, that is bound by a wall 220. In the embodiments of FIGS. 6-10, the wall 220 is transparent and does not include a separate distinct window as illustrated in the embodiments of FIGS. 4-5. In FIGS. 6-10, a beam of energy 300, such as IR, NIR, or UV energy, is transmitted into the conduit 260 through the wall 220 from a first side 301 of the conduit 260. The beam of energy 300 interacts with the infusate 280 and any foreign matter. For example, different portions or wavelength ranges of the beam of energy 300 may be absorbed, refracted or reflected. In certain embodiments, a resulting beam of energy passes through the conduit 260 and to the opposite second side 302 of the conduit 260. In other embodiments, a resulting beam of energy reflects from the conduit 260 back to the first side 301 of the conduit 260.

Figure 6:
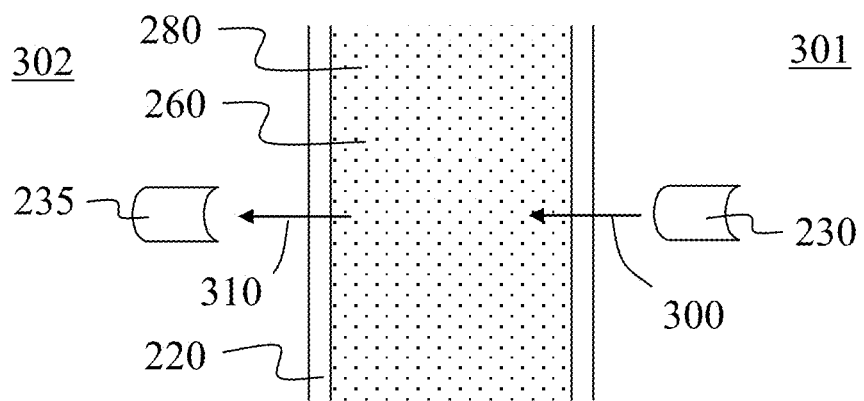
FIGS. 6-10 depict schematic diagrams of the operation of the apparatus for examining a fluid of FIG. 4 or 5 in accordance with embodiments herein.

Referring now to FIG. 6, an embodiment is illustrated in which a transmitter element 230 is located on the first side 301 of the conduit 260 and the receiver element 235 is located on the second side 302 of the conduit 260. The transmitter element 230 transmits a beam of energy through the wall 220 and into the conduit 260 into contact with the infusate 280. As described above, the beam of energy 300 interacts with the infusate 280 and a resulting beam of energy 310 passes through the conduit 260 and exits to the second side 302 of the conduit 260. As shown, the resulting beam of energy 310 is received by receiver element 235 as a signal. The signal can be analyzed as described below in relation to FIG. 11 to determine the composition and concentration of the infusate 280 and whether foreign matter is present in the infusate 280.

Figure 7:
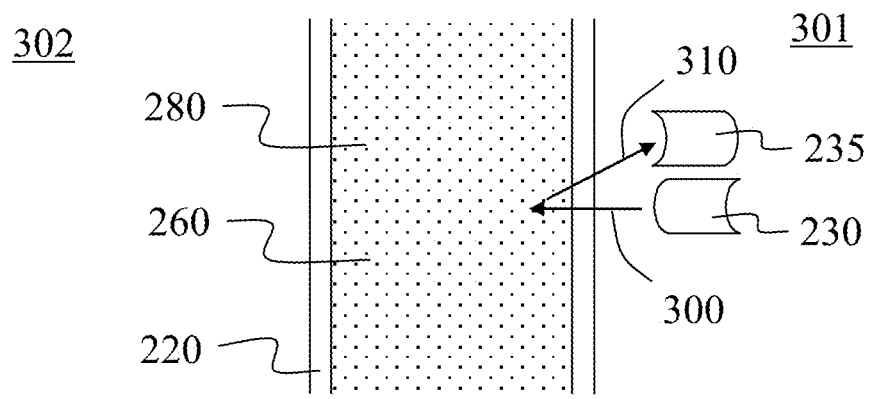

FIG. 7 illustrates an embodiment in which both the transmitter element 230 and the receiver element 235 are located on the first side 301 of the conduit 260. In FIG. 7, the transmitter element 230 transmits the beam of energy 300 through the wall 220 and into the conduit 260 into contact with the infusate 280. The beam of energy 300 interacts with the infusate 280 and a resulting beam of energy 310 is reflected back out of the conduit and to the first side 301 of the conduit 260. As shown, the resulting beam of energy 310 is received by receiver element 235 as a signal and can be analyzed as described below. It is contemplated that an embodiment may use both an opposite side receiver element 235 of FIG. 6 and a same side receiver element 235 of FIG. 7 for receiving the resulting beam of energy 310.

Figure 8:
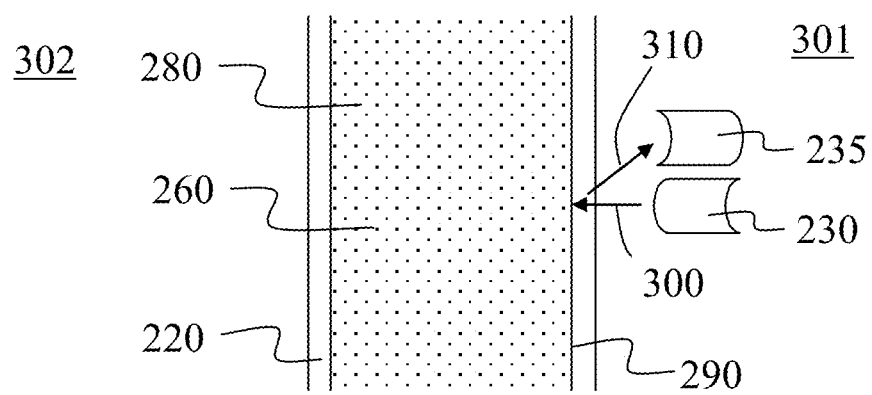

FIG. 8 illustrates a similar structural arrangement as FIG. 7. However, in FIG. 8, it is contemplated that the beam of energy 300 transmitted by transmitter element 230 is reflected by the infusate 280 at the interface 290 of the infusate 280 and the wall 220. As shown, the reflected beam of energy 310 passes back through the wall 220 and is received by the receiver element 235 as a signal for analysis.

Figure 9:
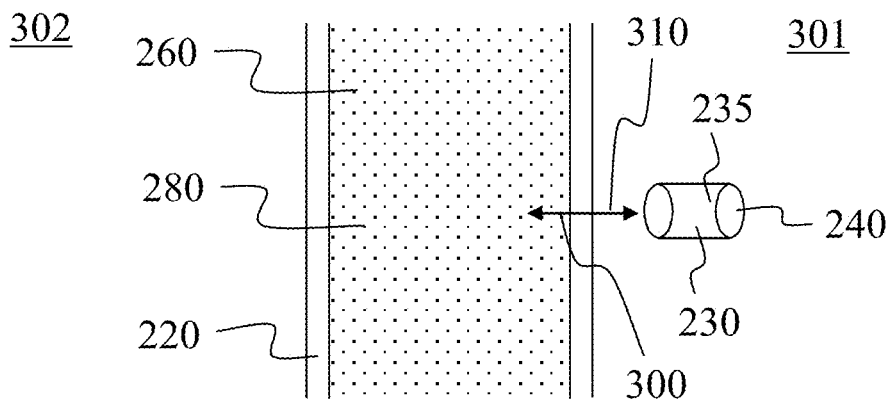
Figure 10:
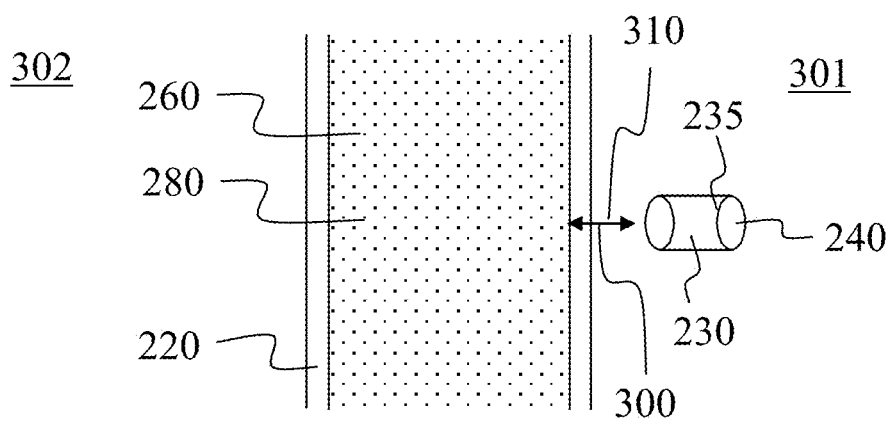

FIGS. 9 and 10 illustrate a transceiver 240 including a transmitter element 230 and receiver element 235. Necessarily, the transmitter element 230 and receiver element 235 are each located on the first side 310 of the conduit 260. In FIG. 9, the transmitter element 230 transmits the beam of energy 300 through the wall 220 and into the conduit 260 into contact with the infusate 280. The beam of energy 300 interacts with the infusate 280 and a resulting beam of energy 310 is reflected back out of the conduit and to the first side 301 of the conduit 260. As shown, the resulting beam of energy 310 is received by receiver element 235 as a signal for analysis.

FIG. 10 illustrates a similar structural arrangement as FIG. 9. In FIG. 10, it is contemplated that the beam of energy 300 transmitted by transmitter element 230 is reflected by the infusate 280 at the interface 290 of the infusate 280 and the wall 220. As shown, the reflected beam of energy 310 passes back through the wall 220 and is received by the receiver element 235 as a signal for analysis.

It is contemplated that an embodiment may use one or more arrangements of transmitter elements 230, receiver elements 235, and/or transceivers 240 of FIGS. 6-10, such as with both same side and opposite side receiver elements 235 for receiving the resulting beam of energy 310.

After the signal of the resulting beam of energy 310 is received by the receiver element 235 in FIGS. 6-10, analysis is performed to identify the composition of the infusate 280, the concentration of the infusate, and/or the presence of foreign matter in the infusate 280. For example, spectroscopic analysis may be performed and compared to a library of known spectral signatures.

Figure 11:
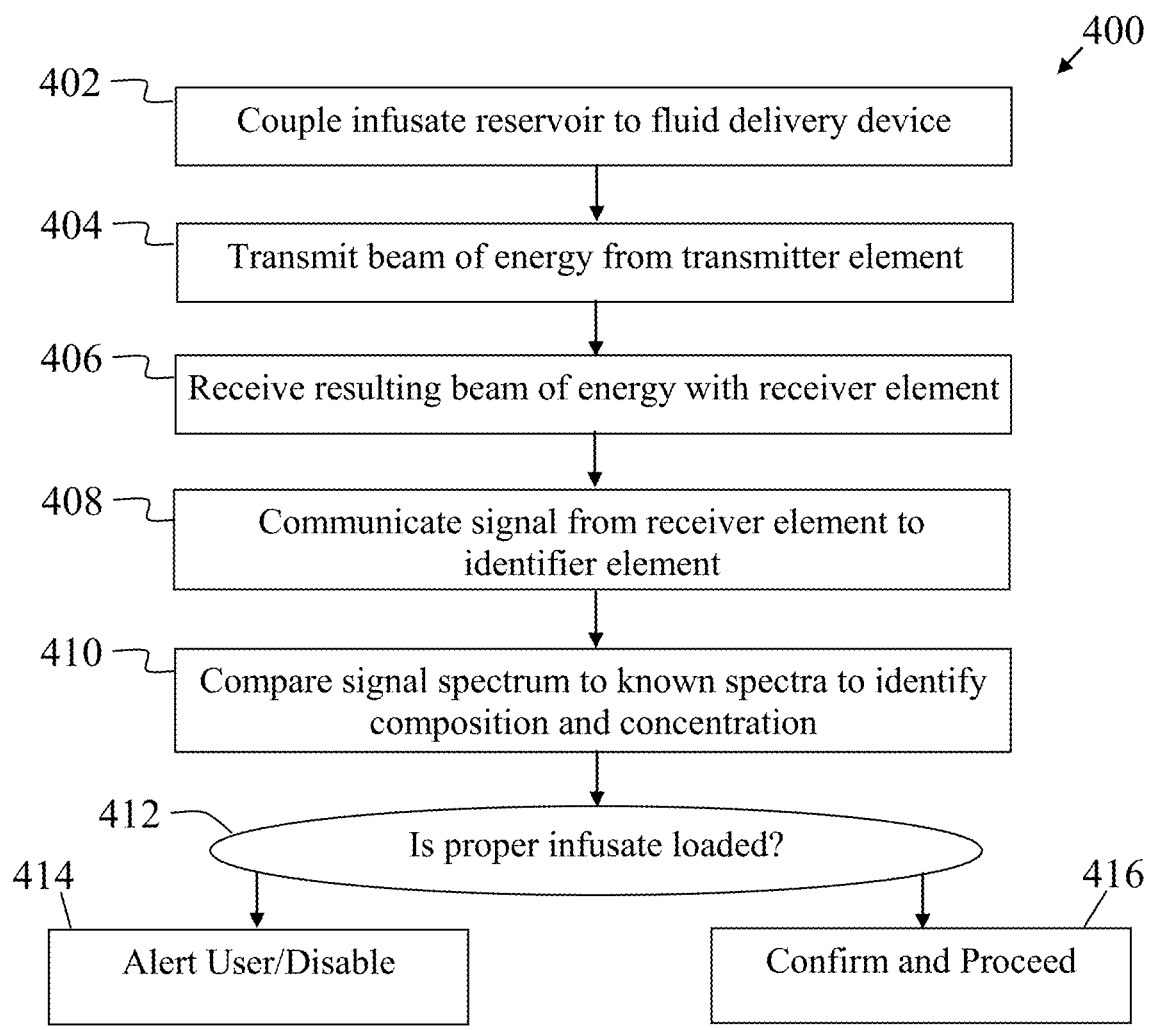
FIG. 11 is a flow chart illustrating a method for identifying a fluid for delivery in accordance with an embodiment.

FIG. 11 illustrates an exemplary method 400 for identifying a fluid for delivery to a body of a user. As shown, an infusate reservoir or other container with a conduit holding an infusate is coupled to a fluid delivery device at step 402. Upon coupling, the identification process may be initiated to confirm that the correct infusate is loaded in the fluid delivery device. Alternatively, the identification process may be initiated when fluid is forced out of the reservoir and through a testing location elsewhere in the fluid conduit. For example, at step 404, a beam of energy is transmitted from the transmitter element into the conduit holding the infusate. The beam of energy interacts with the infusate and exits the conduit as a resulting beam of energy. As used herein, a beam of energy reflected at the interface of the conduit and wall bounding the conduit is considered to have passed through the wall and exits the conduit upon reflection with the interface. At step 406, the resulting beam of energy is received by the receiver element.

At step 408, the signal of the resulting beam of energy is communicated from the receiver element to an identifier element. For example, the signal may be wirelessly communicated from the receiver element to the identifier element. The identifier element may be contained within a PCB, sensing arrangement, CCD or computer. The signal is or includes spectroscopic data that may be represented by a spectrum that may be plotted as a graph of energy absorbance (or transmittance) on the vertical axis vs. frequency or wavelength on the horizontal axis.

Figure 12:
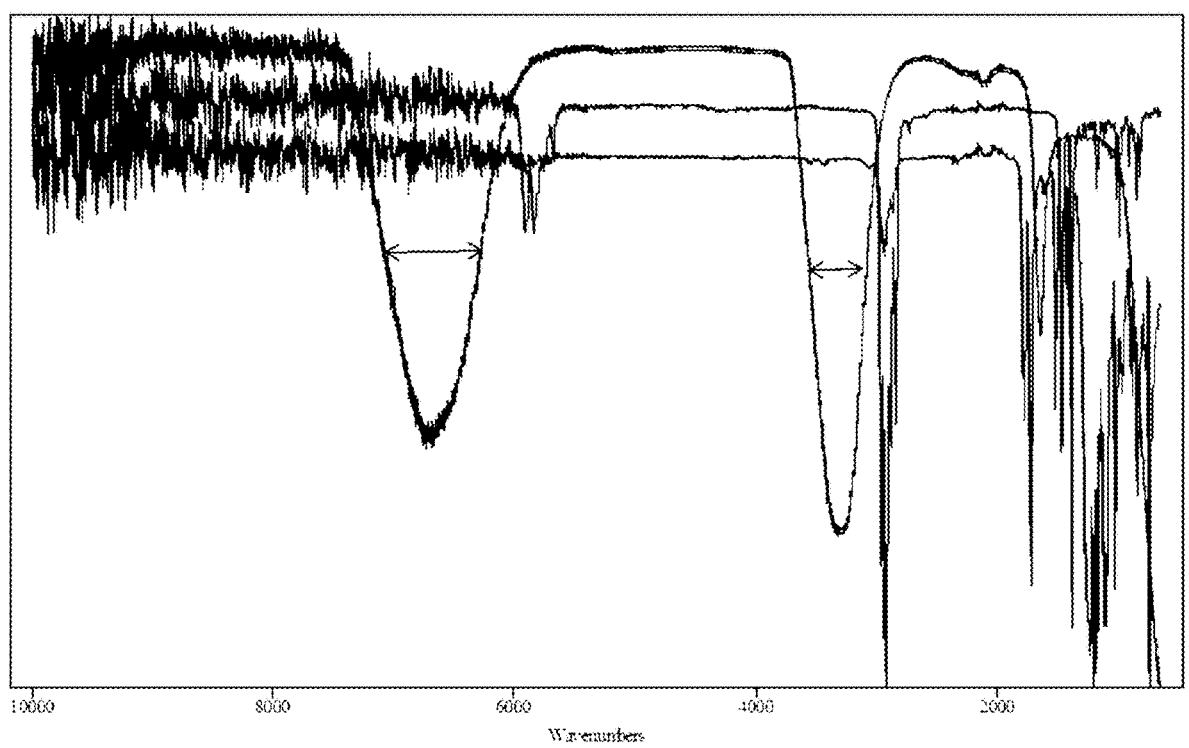
FIG. 12 is an overlapped reflective NIR/IR spectra graph of fluid-path materials and infusates.

The identifier element includes or is coupled to a memory storage or library of spectra of known, i.e., previously tested compositions and concentrations. The memory stores data associated with selected fluids for comparison with detected characteristics of the signal. At step 410, the spectrum of the signal is compared to the spectra of known compositions and concentrations. For example, the identifier element may use the stored data to identify the infusate based on the received signal. As is known in absorptive spectroscopic analysis, different compositions and different concentrations of those compositions exhibit unique spectra or signature spectra. For example, differing values of intensity of radiation at specific wavelengths or frequencies or over specific ranges of wavelengths or frequencies may indicate that the beam of energy passed through a specific concentration of a specific composition. As an example, a reflective NIR/IR spectra graph of fluid-path materials and infusates (insulin formulations) is presented in FIG. 12, in which the spectral different regions may be used for infusate/bubble tracking. In the exemplary embodiment of FIG. 12, reflective NIR/IR spectra of fluid-path materials and infusates indicate that there are two NIR regions (around 1.7 μm or around 3 μm) that may be used for infusate tracking inside the polymeric component (reservoir, p-cap, or tubing). Spectroscopic signals at various wavelengths may be orthogonally used for better identification accuracy.

At step 412, the method queries whether, based on the signal spectrum comparison, the proper or expected infusate is loaded in the fluid delivery device. If not, the PCB, sensing arrangement, CCD or computer may automatically alert the user and/or disable infusion of the infusate from the fluid delivery device at step 414. On the other hand, if the correct infusate is loaded, the PCB, sensing arrangement, CCD or computer may confirm that the correct infusate is loaded and allow the fluid delivery device to proceed with an infusion process at step 416.

While the subject matter is described above primarily in the context of a pre-loaded reservoir containing insulin reservoir for regulating a glucose level of a user, the subject matter described herein is not limited to any type of media dispensed from or otherwise provided by the reservoir, and the subject matter may be implemented with other medical devices or electronic devices other than fluid infusion devices. For example, any electronic device could be configured to analyze and identify the composition and concentration of a fluid contained in a conduit through transmission of a beam of energy and processing of the resulting signal through spectroscopic analysis.

For the sake of brevity, conventional techniques related to glucose sensing and/or monitoring, closed-loop glucose control, sensor calibration, electrical signals and related processing, electrical interconnects or interfaces, packaging, fluid communications, fluid monitoring or measuring, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method for identifying a fluid for delivery to a body of a user, the method comprising:
    holding a first fluid in a reservoir;
    coupling the reservoir to a device housing having a conduit;
    coupling the device housing to an infusion device with a connector, wherein the connector comprises:
        a coupling directly connected to the reservoir to establish fluid communication from the reservoir to the conduit;
        a wall having an internal surface and an external surface, wherein the internal surface bounds the conduit;
        a transmitter element mounted on the connector;
        a receiver element mounted on the connector; and
        an identifier element mounted on the connector and coupled to the receiver element;
    directing flow of the first fluid through the conduit;
    transmitting an initial beam of energy from the transmitter element into contact with the first fluid;
    altering the initial beam of energy through interaction with the first fluid by absorbing, refracting and/or reflecting the beam of energy to create a first altered beam of energy, wherein the first altered beam of energy is different from the initial beam of energy;
    receiving the first altered beam of energy with the receiver element; and
    analyzing the first altered beam to identify the first fluid with the identifier element.

2. The method of claim 1 wherein analyzing the first altered beam to identify the fluid comprises comparing the first altered beam of energy with stored data associated with selected fluids to identify the first fluid.

3. The method of claim 1 wherein transmitting the initial beam of energy comprises transmitting a beam of infrared light or near infrared light.

4. The method of claim 1 further comprising:
    replacing the first fluid with a second fluid;
    directing flow of the second fluid through the conduit;
    transmitting the initial beam of energy from the transmitter element into contact with the second fluid;
    altering the initial beam of energy through interaction with the second fluid by absorbing, refracting and/or reflecting the beam of energy to create a second altered beam of energy, wherein the second altered beam of energy is different from the initial beam of energy and is different from the first altered beam of energy;
    receiving the second altered beam of energy with the receiver element; and
    analyzing the second altered beam to identify the second fluid with the identifier element.

5. The method of claim 4 wherein the initial beam of energy is not associated with the first fluid or with the second fluid.

6. The method of claim 1 wherein the initial beam of energy is not associated with the first fluid.

7. The method of claim 1 further comprising securing the device housing to skin of the user.

8. The method of claim 7 further comprising:
    while the device housing is secured to the skin of the user, replacing the first fluid with a second fluid;
    directing flow of the second fluid through the conduit;
    transmitting the initial beam of energy from the transmitter element into contact with the second fluid;
    altering the initial beam of energy through interaction with the second fluid by absorbing, refracting and/or reflecting the beam of energy to create a second altered beam of energy, wherein the second altered beam of energy is different from the initial beam of energy and is different from the first altered beam of energy;
    receiving the second altered beam of energy with the receiver element; and
    analyzing the second altered beam to identify the second fluid with the identifier element.

9. The method of claim 7 wherein the reservoir is a first reservoir, and wherein the method further comprises:
    while the device housing is secured to the skin of the user, replacing the first reservoir with a second reservoir containing a second fluid;
    directing flow of the second fluid through the conduit;
    transmitting the initial beam of energy from the transmitter element into contact with the second fluid;
    altering the initial beam of energy through interaction with the second fluid by absorbing, refracting and/or reflecting the beam of energy to create a second altered beam of energy, wherein the second altered beam of energy is different from the initial beam of energy and is different from the first altered beam of energy;
    receiving the second altered beam of energy with the receiver element; and
    analyzing the second altered beam to identify the second fluid with the identifier element.

* * * * *